(12) United States Patent
Petigard et al.

(10) Patent No.: US 6,417,211 B1
(45) Date of Patent: Jul. 9, 2002

(54) ISOTHIAZOLONE CONCENTRATES

(75) Inventors: Ramesh Balubhai Petigard, Hatfield; Christine Elizabeth Garrett, Bensalem, both of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/629,223

(22) Filed: Jul. 31, 2000

Related U.S. Application Data

(60) Provisional application No. 60/151,507, filed on Aug. 30, 1999.

(51) Int. Cl.$^7$ .................. A01N 43/80; A61K 31/425
(52) U.S. Cl. .................................... 514/372
(58) Field of Search .............................. 514/372

(56) References Cited

U.S. PATENT DOCUMENTS

| | | |
|---|---|---|
| 5,142,058 A | 8/1992 | Willingham et al. |
| 5,756,005 A | 5/1998 | Ghosh et al. |
| 5,910,503 A | 6/1999 | Mattox et al. |

FOREIGN PATENT DOCUMENTS

| | | | |
|---|---|---|---|
| EP | 476943 | * | 3/1992 |
| EP | 988789 | * | 3/2000 |
| JP | 05163107 | * | 6/1993 |
| JP | 06092806 | * | 4/1994 |
| JP | 09067212 | * | 3/1997 |

* cited by examiner

*Primary Examiner*—Alton Pryor
(74) *Attorney, Agent, or Firm*—Thomas J. Howell

(57) ABSTRACT

Stable liquid microbicide compositions, having high concentrations of non-halogenated 3-isothiazolones, are disclosed. Aqueous concentrates containing from 60 to 95% non-halogenated 3-isothiazolones provide excellent low temperature storage stability and good chemical stability, thus allowing enhanced flexibility in the preparation of less concentrated antimicrobial formulations.

15 Claims, No Drawings

ISOTHIAZOLONE CONCENTRATES

This application claims benefit of Ser. No. 60/151,507 filed Aug. 30, 1999.

BACKGROUND

This invention relates to highly concentrated solutions of isothiazolones, in particular, 2-methyl-3-isothiazolone, in water, and their preparation.

Microbicides are used commercially to prevent the growth of microbes in a variety of environments, such as cooling towers, metal working fluid systems, latices (such as paints) and cosmetics. One of the more important classes of microbicides is 3-isothiazolones. Many 3-isothiazolones have achieved commercial success because they are very effective in preventing microbial growth under a wide variety of conditions. Among the most important 3-isothiazolones are the water-soluble isothiazolones, such as 2-methyl-3-isothiazolone.

While 3-isothiazolones are very effective microbicides, they suffer from being unstable under certain conditions. Without the presence of a stabilizer, many 3-isothiazolones chemically degrade and lose microbicidal efficacy. Much research has been devoted to stabilizing 3-isothiazolones, especially with regard to aqueous formulations of 3-isothiazolones, that is, where the concentration of active ingredient in the solution is from about 5 to about 35% by weight (typically 12 to 15%); see U.S. Pat. No. 5,910,503. These solutions typically require the use of stabilizers, such as, for example, nitrate salts and copper salts. Organic compound stabilizers are also used for protecting 3-isothiazolones in antagonistic environments; see U.S. Pat. No. 5,142,058. Up until now, the concentration of active ingredient (3-isothiazolone) in aqueous concentrate compositions provided to formulators has been in the aforementioned range of 5 to 35% (typically 12 to 15%), or up to about 50% in the case of certain organic solvent (such as propylene glycol) concentrates. (see U.S. Pat. No. 5,756,005).

The problem addressed by the present invention is to overcome the difficulties of using conventional microbicide solutions (for example, 5 to 50% concentration of active ingredient) or solid technical grade materials where (a) the relatively low concentration of active ingredient in conventional aqueous concentrates severely limits the range of dilutions that the formulator can consider and (b) the solid technical grade materials require additional processing, for example, melting of the solid, with possible consequent product degradation and darkening.

STATEMENT OF INVENTION

The present invention provides a stable liquid microbicide composition comprising (a) 60 to 95 percent, based on the weight of the composition, of at least one water-soluble, non-halogenated 3-isothiazolone; and (b) 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound.

In another embodiment, the present invention provides a method for preparing a stable liquid microbicide composition comprising combining (a) from 60 to 95 percent, based on weight of the composition, of at least one water-soluble, non-halogenated 3-isothiazolone; and (b) from 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound; wherein the liquid microbicide composition remains homogeneous and fluid at temperatures of 20 to 25° C. for at least 24 hours.

In a further embodiment, the present invention provides a method for preparing formulated microbicide solutions, comprising combining from 0.005 to 1 part, by weight, of the aforementioned liquid microbicide composition with 1 part, by weight, of a compatible diluent.

DETAILED DESCRIPTION

We have discovered that non-halogenated 3-isothiazolone concentrate compositions can be prepared at active ingredient (3-isothiazolone) concentrations in excess of 50 percent, based on total weight of the composition, while maintaining both physical and chemical stability of the liquid concentrate. We have discovered that mixtures of specific 3-isothiazolones and specific solvents used in specific relative proportions unexpectedly provide the stable, highly concentrated, non-halogenated 3-isothiazolone solutions of the present invention.

As used throughout this specification, the following terms shall have the indicated meanings, unless the context clearly indicates otherwise. The term "microbicide" refers to a compound capable of inhibiting the growth of or controlling the growth of microorganisms in a certain environment. The term "water-miscible" refers to compatibility with or solubility in a formulation upon dilution with aqueous media, such as may be used by formulators. As used in this specification, the following abbreviations are applied: HPLC=high performance liquid chromatography; C=centigrade. All amounts are percent (%) by weight, unless otherwise noted and all percent by weight ranges are inclusive; all ratios are by weight and all ratio ranges are inclusive.

Any water soluble, non-halogenated 3-isothiazolone (NHITA) compound is useful in the compositions of the present invention. Water soluble NHITA compounds are those having a water solubility greater than 5%. Suitable NHITA compounds include, for example, substituted and unsubstituted 2-($C_1$–$C_4$)alkyl-3-isothiazolones, where the substituted isothiazolones may contain ($C_1$–$C_4$)alkyl groups at one or both of the 4- and 5-positions of the isothiazolone ring. Specific NHITA compounds include, for example, 2-methyl-3-isothiazolone, 2-ethyl-3-isothiazolone, 2-propyl-3-isothiazolone, 2-isopropyl-3-isothiazolone, 2-butyl-3-isothiazolone (includes 2-n-butyl-, 2-isobutyl- and 2-secbutyl-derivatives). Preferably, the NHITA compound is 2-methyl-3-isothiazolone.

The stable liquid microbicide compositions of the present invention typically contain 60 to 95%, preferably 70 to 95%, more preferably 75 to 94%, and most preferably from 80 to 90% NHITA, based on weight of the composition.

The amount of solvent useful in the stable liquid microbicide compositions of the present invention is typically from 5 to 40%, preferably 5 to 30%, more preferably 10 to 25%, and most preferably from 10 to 20%, based on weight of the composition.

Solvents suitable for use in the compositions of the present invention include, for example, water and water-miscible organic solvents. Suitable water-miscible solvents include, ($C_1$–$C_4$)alkanols, such as, for example, methanol, ethanol, 1-propanol, 2-propanol and isobutyl alcohol; ($C_2$–$C_8$)alkoxy/hydroxy compounds, such as, for example, 2-methoxyethanol, 2-butoxyethanol, 2-(2-butoxyethoxyl) ethanol, phenoxyethanol, benzyl alcohol, phenethyl alcohol, ethylene glycol, 1,2-dimethoxyethane, diethylene glycol, propylene glycol, dipropylene glycol and glycerine; and ($C_2$–$C_4$)aprotic compounds, such as, for example, dimethyl sulfoxide, diethyl carbonate and propylene carbonate. Preferably, the solvent is water. When used, the water-miscible organic solvent is preferably selected from 2-propanol, ethylene glycol and propylene glycol. Mixtures of water and one or more water-miscible solvents, as well as mixtures of one or more water-miscible solvents in the absence of water, may also be used.

An advantage of the compositions of the present invention is that they are both physically and chemically stable as prepared and upon storage. That is, these highly concentrated solutions of NHITA remain physically stable upon storage and do not settle, separate or precipitate into different phases. By "physically stable" we mean that the compositions are homogeneous and fluid at temperatures of 20 to 25° C. for at least 24 hours. Preferably the compositions are physically stable at 20° C. and below for at least 3 days, more preferably for at least 2 weeks, and most preferably for at least 4 weeks. In addition, it is desirable that the compositions retain their physical stability for similar time periods at temperatures of 15° C. and below, and preferably at 5° C. and below.

In addition, the liquid microbicide compositions of the present invention are chemically stable, that is, they require no "stabilizing" agents to prevent the chemical decomposition of the 3-isothiazolone compounds. By "chemically stable" we mean that the active ingredient (non-halogenated 3-isothiazolone) retains at least 90%, preferably at least 95% and more preferably at least 98%, of its initial active ingredient concentration for at least 10 days and preferably for at least 30 days, at ambient conditions (20 to 25° C.). It is also desirable that the compositions retain their chemical stability for similar time periods at temperatures above 25° C. and preferably up to about 55° C. Typical 3-isothiazolone stabilizers include, for example, metal salts, such as, for example, iodate, bromate, nitrate and copper salts. The presence of metal salts in conventional 3-isothiazolone concentrates (12 to 15% active ingredient) is often undesirable in many end use applications, such as, in latices where precipitation, coagulation or phase separation may occur because of the salt stabilizer. Although not required, limited amounts of metal salts may be added to the liquid microbicide compositions of the present invention. However, preferably the composition is substantially free of metal salt; that is, zero or up to 0.5 percent, preferably zero or up to 0.1% and more preferably zero or up to 0.001%, of metal salt may be present, based on weight of the composition.

The liquid microbicide compositions of the present invention can be used to inhibit the growth of microorganisms by introducing a microbicidally effective amount of the compositions onto or into an environment subject to microbial attack. Typical environments include, for example, cooling towers, air washers, boilers, mineral slurries, wastewater treatment, ornamental fountains, reverse osmosis filtration, ultrafiltration, ballast water, evaporative condensers, heat exchangers, pulp and paper processing fluids, plastics, emulsions and dispersions, paints, latices, coatings (such as varnishes), construction products (such as mastics, caulks, and sealants), construction adhesives (such as ceramic adhesives, carpet backing adhesives, and laminating adhesives), industrial or consumer adhesives, photographic chemicals, printing fluids, household products (such as bathroom disinfectants or sanitizers), cosmetics and toiletries, shampoos, soaps, detergents, industrial disinfectants or sanitizers (such as cold sterilants and hard surface disinfectants), floor polishes, laundry rinse water, metalworking fluids, conveyor lubricants, hydraulic fluids, leather and leather products, textiles, textile products, wood and wood products (such as plywood, chipboard, flakeboard, laminated beams, oriented strandboard, hardboard and particleboard), petroleum processing fluids, fuel, oilfield fluids (such as injection water, fracture fluids and drilling muds), agriculture adjuvant preservation, surfactant preservation, medical devices, diagnostic reagent preservation, food preservation (such as plastic or paper food wrap), pools and spas. The liquid microbicide compositions of present invention are especially useful in the following environments: cooling towers, boilers, wastewater treatment, reverse osmosis filtration, evaporative condensers; heat exchangers, pulp and paper processing fluids, emulsions and dispersions, paints, latices, and metal working fluids.

The amount of microbicide suitable to inhibit or control the growth of microorganisms is well known in the art and depends upon the environment to be protected. Up until now, the formulator was required to use a 5 to 35% (typically 12 to 15%) aqueous concentrate of active ingredient or a "technical" grade of solid active ingredient (typically at least 90% and preferably at least 95% purity) in preparing final end use antimicrobial formulations. The relatively low concentration of active ingredient available in conventional aqueous concentrates severely limits the range of dilutions (concentration and solvent type) that the formulator could consider. Solid technical grade microbicides, although allowing for a greater range of dilution concentrations being available, require melting of the solid material (for example, 2-methyl-3-isothiazolone melts at temperatures of 45–55° C.), making the microbicide subject to degradation and darkening. Thus, the liquid microbicide compositions of the present invention containing 60 to 95% active ingredient offer a great advantage to the formulator because (a) equipment for melting of technical grade material is no longer required and (b) a greater range of final solvent and concentration dilutions is attainable versus using the conventional active ingredient concentrates.

Typically, the stable liquid microbicide compositions of the present invention may be used by the formulator in the following manner to prepare microbicidal formulations: from 0.005 to 1 part, preferably from 0.01 to 0.5 part and more preferably from 0.1 to 0.2 part, by weight, of the liquid microbicide composition (60 to 95% active ingredient) is combined with 1 part of a compatible diluent. Suitable diluents include, for example, those previously described; that is, water, ($C_1$–$C_4$)alkanols, water-miscible ($C_2$–$C_8$) alkoxy/hydroxy compounds and water miscible ($C_2$–$C_4$) aprotic compounds, and other diluents compatible with the liquid microbicide concentrate. In addition, the diluents may contain optional ingredients, including other antimicrobial agents, useful to the formulator.

Optionally, other antimicrobial agents may be present in the liquid microbicide compositions of the present provided that the physical and chemical stability of the composition is substantially unaffected. For example, limited amounts of halogenated 3-isothiazolones, such as, for example, 5-chloro-2-methyl-3-isothiazolone (CMI), may be present. Preferably the composition is substantially free of halogenated 3-isothiazolone; that is, zero or up to 3%, preferably zero or up to 1% and more preferably zero or up to 0.5%, of halogenated 3-isothiazolone may be present, based on combined weight of halogenated 3-isothiazolone and non-halogenated 3-isothiazolone. Other suitable antimicrobial agents that may be present in the liquid microbicide compositions include, for example, 3-iodo-2-propynylbutylcarbamate, 2-bromo-2-nitropropanediol, glutaric dialdehyde, 2-n-octyl-3-isothiazolone, sodium 2-pyridinethiol-1-oxide, p-hydroxy benzoic acid alkyl ester, tris(hydroxymethyl)nitromethane, dimethylol-dimethyl-hydantoin and benzisothiazolone. Preferably the composition is substantially free of other antimicrobial agents; that is, zero or up to 20%, preferably zero or up to 5%, and more preferably zero or up to 1%, of other antimicrobial agents may be present, based on the weight of the composition.

Some embodiments of the invention are described in detail in the following Examples. All ratios, parts and percentages are expressed by weight unless otherwise specified, and all reagents used are of good commercial quality unless otherwise specified. Abbreviations used in the Examples and Tables are listed below with the corresponding descriptions.

| MeOH | = | Methanol |
|---|---|---|
| PG | = | Propylene Glycol |
| DPG | = | Dipropylene Glycol |
| IPA | = | Isopropanol |
| φCH$_2$OH | = | Benzyl alcohol |
| φOCH$_2$CH$_2$OH | = | Phenoxyethanol |
| BEE | = | 2-(2-Butoxyethoxyl)ethanol |
| DEC | = | Diethyl Carbonate |
| PC | = | Propylene Carbonate |
| DME | = | 1,2-Dimethoxyethane |
| CMI | = | 5-Chloro-2-methyl-3-isothiazolone |
| MI | = | 2-Methyl-3-isothiazolone |
| NA | = | Not Analyzed |

EXAMPLE 1

Samples of technical grade 2-methyl-3-isothiazolone (MI) were used to prepare solutions of the NHITA in various solvents at different concentrations. The technical grade MI was typically 95 to 98% pure. Solutions were prepared by adding a weighed amount of molten MI (melted at about 55° C.) to a weighed amount of deionized water (or a solvent or a solvent-water mixture) in a 20-milliliter (ml) vial; the mixture was swirled and allowed to cool to room temperature. The prepared samples were allowed to stand at room temperature (20–25° C.) for 24 hours and then subjected to storage at cooler temperatures (5° C. and −17° C.) for at least 72 hours; observations were made at each condition to determine physical stability (homogeneity, clarity, crystallization, precipitation, phase separation). The samples were considered physically stable if no crystallization, phase separation or precipitation occurred; concentrations (or concentration ranges) at which the compositions were unstable are indicated by ** superscript, otherwise concentrations (ranges) listed were stable; results are summarized in Table I (concentrations are weight % MI). In addition to the data in Table I, 80% and 90% MI solutions in water were stable for at least 4 months at 5° C. Exemplification of chemical stability is shown in Table II.

TABLE I (Physical Stability)

| | Storage Temperature | | |
|---|---|---|---|
| Solvent System | 20–25° C. | 5° C. | −17° C. |
| Water | 60–94.4; 95.4** | 60–89.5; 90.5** | 70–77; 88** |
| 50/50 MeOH/Water | 88 | 88 | 88** |
| MeOH | 78–88 | 78; 88** | 78 |
| PG | 68–88 | 68; 78–88** | 68 |
| DPG | 75–90 | 75–90** | NA |
| IPA | 78–88 | 78; 88** | 78** |
| φCH$_2$OH | 60 | 60 | 60** |
| φOCH$_2$CH$_2$OH | 60 | 60 | 60** |
| BEE | 68–88 | 68–88** | NA |
| DEC | 70; 80–90** | 70** | NA |
| DMSO | 70–80; 90** | 70–80** | NA |
| DME | 70–80; 90** | 70–80** | NA |
| PC | 69; 80–90** | 69** | NA |

** = physically unstable, crystal formation or insoluble

TABLE II (Chemical Stability)

| Initial MI Concentration* | Solvent System | Storage Condition | % Active Ingredient (MI) Remaining* |
|---|---|---|---|
| 85.8 | Water | 55° C./4 weeks | 97.1 |
| 68 | PG | 40° C./11 days | 100 |
| 78 | MeOH | 40° C./11 days | 104 |
| 88 | 50/50 MeOH/Water | 40° C./11 days | 101 |

*based on HPLC analysis, ± 1–2%

We claim:

1. A stable liquid microbicide composition consisting essentially of:
   (a) 60 to 95 percent, based on the weight of the composition, of at least one water-soluble, non-halogenated 3-isothiazolone; and
   (b) 5 to 40 percent, based on the weight of the composition, of at least one solvent selected from water, (C$_1$–C$_4$)alkanol, water-miscible (C$_2$–C$_8$)alkoxy/hydroxy compound and water-miscible (C$_2$–C$_4$)aprotic compound.

2. The composition of claim 1 wherein the liquid composition is homogeneous and fluid at temperatures of 20 to 25° C. for at least 24 hours.

3. The composition of claim 1 wherein the liquid composition comprises 75 to 94 percent of the water-soluble, non-halogenated 3-isothiazolone.

4. The composition of claim 1 where the water-soluble, non-halogenated 3-isothiazolone is selected from 2-methyl-3-isothiazolone, 2-ethyl-3-isothiazolone, 2-isopropyl-3-isothiazolone and 2-propyl-3-isothiazolone.

5. The composition of claim 1 wherein the water-miscible (C$_2$–C$_8$)alkoxy/hydroxy compound is selected from 2-methoxyethanol, 2-butoxyethanol, 2-(2-butoxyethoxyl)ethanol, phenoxyethanol, benzyl alcohol, phenethyl alcohol, ethylene glycol, 1,2-dimethoxyethane, diethylene glycol, propylene glycol, dipropylene glycol and glycerine.

6. The composition of claim 1 wherein the (C$_1$–C$_4$) alkanol is selected from methanol, ethanol, 1-propanol, 2-propanol and isobutyl alcohol.

7. A method for preparing formulated microbicide solutions, consisting essentially of combining from 0.005 to 1 part, by weight, of the liquid microbicide composition of claim 1, with 1 part, by weight, of a compatible diluent.

8. The composition of claim 1 wherein the ($C_2$–$C_4$)aprotic compound is selected from dimethyl sulfoxide, diethyl carbonate and propylene carbonate.

9. The composition of claim 4 wherein the water-soluble, non-halogenated 3-isothiazolone is 2-methyl-3-isothiazolone and the solvent is water.

10. The composition of claim 9 wherein the 2-methyl-3-isothiazolone is 80 to 90 weight percent.

11. A stable liquid microbicide composition consisting essentially of:
   (a) 60 to 95 percent, based on the weight of the composition, of at least one water-soluble, non-halogenated 3-isothiazolone;
   (b) 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound; and
   (c) up to 3 percent of halogenated 3-isothiazolone, based on combined weight of halogenated 3-isothiazolone and non-halogenated-isothiazolone.

12. A stable liquid microbicide composition consisting essentially of:
   (a) 60 to 95 percent, based on the weight of the composition, of at least one water-soluble, non-halogenated 3-isothiazolone;
   (b) 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound; and
   (c) up to 20 percent, based on weight of the composition, of at least one antimicrobial selected from 3-iodo-2-propynylbutylcarbamate, 2-bromo-2-nitropropanediol, glutaric dialdehyde, 2-n-octyl-3-isothiazolone, sodium 2-pyridinethiol-1-oxide, p-hydroxy benzoic acid alkyl ester, tris(hydroxymethyl)nitromethane, dimethylol-dimethyl-hydantoin and benzisothiazolone.

13. A method for preparing a stable liquid microbicide composition consisting essentially of combining:
   (a) from 60 to 95 percent, based on weight of the composition, of at least one water-soluble, non-halogenated 3-isothiazolone; and
   (b) from 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound;

wherein the liquid microbicide composition remains homogeneous and fluid at temperatures of 20 to 25° C. for at least 24 hours.

14. A method of preparing a stable liquid microbicide composition consisting essentially of combining:
   (a) 60 to 95 percent, based on the weight of the composition, of at least one water-soluble, non-halogenated 3-isothiazolone;
   (b) 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound; and
   (c) up to 20 percent, based on weight of the composition, of at least one antimicrobial selected from 3-iodo-2-propynylbutylcarbamate, 2-bromo-2-nitropropanediol, glutaric dialdehyde, 2-n-octyl-3-isothiazolone, sodium 2-pyridinethiol-1-oxide, p-hydroxy benzoic acid alkyl ester, tris(hydroxymethyl)nitromethane, dimethylol-dimethyl-hydantoin and benzisothiazolone.

15. A method of preparing a stable liquid microbicide composition consisting essentially of combining:
   (a) 60 to 95 percent, based on the weight of the composition, of at least one water-soluble, non-halogenated 3-isothiazolone;
   (b) 5 to 40 percent, based on the weight of the composition, of at least one solvent selected from water, ($C_1$–$C_4$)alkanol, water-miscible ($C_2$–$C_8$)alkoxy/hydroxy compound and water-miscible ($C_2$–$C_4$)aprotic compound; and
   (c) up to 3 percent of halogenated 3-isothiazolone, based on combined weight of halogenated 3-isothiazolone and non-halogenated-isothiazolone.

* * * * *

UNITED STATES PATENT AND TRADEMARK OFFICE
CERTIFICATE OF CORRECTION

PATENT NO. : 6,417,211 B1
DATED : July 9, 2002
INVENTOR(S) : Ramesh Balubhai Petigara et al.

It is certified that error appears in the above-identified patent and that said Letters Patent is hereby corrected as shown below:

<u>Title page,</u>
Item [75], Inventors name is incorrect. The name correction should read
-- Ramesh Balubhai Petigara --.

Signed and Sealed this

Thirty-first Day of December, 2002

JAMES E. ROGAN
*Director of the United States Patent and Trademark Office*